(12) United States Patent
Nadeev et al.

(10) Patent No.: US 9,417,177 B2
(45) Date of Patent: *Aug. 16, 2016

(54) METHOD FOR EXAMINING SAMPLES OF UNCONSOLIDATED POROUS MEDIA

(71) Applicant: SCHLUMBERGER TECHNOLOGY CORPORATION, Sugar Land, TX (US)

(72) Inventors: Alexander Nikolaevich Nadeev, Spring, TX (US); Evgeny Mikhailovich Chuvilin, Moscow (RU); Olga Vladimirovna Popova, Moscow (RU)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 159 days.

This patent is subject to a terminal disclaimer.

(21) Appl. No.: 14/361,631

(22) PCT Filed: Nov. 28, 2012

(86) PCT No.: PCT/RU2012/000983
§ 371 (c)(1),
(2) Date: May 29, 2014

(87) PCT Pub. No.: WO2013/095192
PCT Pub. Date: Jun. 27, 2013

(65) Prior Publication Data
US 2014/0334690 A1    Nov. 13, 2014

(30) Foreign Application Priority Data

Dec. 20, 2011 (RU) ................................ 2011151772

(51) Int. Cl.
*G01N 1/42* (2006.01)
*G01N 15/08* (2006.01)
(Continued)

(52) U.S. Cl.
CPC .............. *G01N 15/0227* (2013.01); *G01N 1/42* (2013.01); *G01N 15/08* (2013.01); *G01N 1/28* (2013.01);
(Continued)

(58) Field of Classification Search
CPC .............. A61B 6/00; A61B 6/02; A61B 6/03; A61B 6/032; A61B 6/48; A61B 6/481; A61B 6/488; G01N 1/00; G01N 1/28; G01N 1/42; G01N 2001/1062; G01N 2001/1068; G01N 2001/1081; G01N 15/00; G01N 15/02; G01N 15/0205; G01N 15/0227; G01N 15/08; G01N 23/00; G01N 23/02; G01N 23/04; G01N 23/046; G01N 23/06; G01N 23/08; G01N 23/083; G01T 1/00; G01T 1/16; G01T 1/20; G01T 1/24; G01T 3/008
See application file for complete search history.

(56) References Cited

U.S. PATENT DOCUMENTS 3,941,191 A    3/1976  Pusch
4,587,857 A    5/1986  Bush
(Continued)

FOREIGN PATENT DOCUMENTS

RU    2316754 C1    2/2008

OTHER PUBLICATIONS

Bruker, "Cooling Stage", Retrieved on Mar. 28, 2016, http://www.skyscan.be/products/stages.htm, 2 pages.
(Continued)

*Primary Examiner* — Anastasia Midkiff

(57) ABSTRACT

A sample of an unconsolidated porous medium is frozen and at subzero temperature is placed into contact with a frozen solution of an X-ray contrast agent. Upon the end of saturation of the sample, X-ray computed microtomography of the sample is conducted at subzero temperatures and by means of analyzing the obtained computer tomograhic image, spatial distribution and concentration of ice and/or gas hydrate inclusions, open and closed porosity, pore size distribution, specific surface in the sample are determined.

10 Claims, 1 Drawing Sheet

(51) Int. Cl.
    *G01N 23/04*     (2006.01)
    *G01N 1/28*     (2006.01)
    *G01N 15/02*     (2006.01)
    *G01N 1/10*     (2006.01)

(52) U.S. Cl.
    CPC ............ *G01N 15/088* (2013.01); *G01N 23/046* (2013.01); *G01N 2001/1068* (2013.01); *G01N 2015/0833* (2013.01); *G01N 2015/0846* (2013.01); *G01N 2223/419* (2013.01); *G01N 2223/616* (2013.01); *G01N 2223/649* (2013.01)

(56) References Cited

U.S. PATENT DOCUMENTS

| | | |
|---|---|---|
| 4,649,483 A | 3/1987 | Dixon |
| 4,722,095 A | 1/1988 | Muegge et al. |
| 4,982,086 A | 1/1991 | Withjack |
| 5,027,379 A | 6/1991 | Hunt et al. |
| 5,359,194 A | 10/1994 | Moss |
| 5,469,488 A | 11/1995 | Ono |
| 2005/0010106 A1 | 1/2005 | Lang et al. |
| 2006/0068373 A1* | 3/2006 | Bose ........................ G01N 1/42 435/4 |
| 2014/0328449 A1 | 11/2014 | Nadeev et al. |

OTHER PUBLICATIONS

Chuvilin, "Migration of ions of chemical elements in frozen soils and ice", Jan. 1999, Polar Record, vol. 35, Issue 192, pp. 59-66.

Kneafsey, et al., "Examination of core samples from the Mount Elbert Gas Hydrate Stratigraphic Test Well, Alaska North Slope: Effects of retrieval and preservation", 2011, Marine and Petroleum Geology, vol. 28, No. 2, pp. 381-393.

Torrance, et al., "X-ray computed tomography of frozen soil", Jun. 2008, Cold Regions Science and Technology, vol. 53, Issue 1, pp. 75-82.

Torsaeter, et al., "The Effect of Freezing of Slightly Consolidated Cores", Sep. 1987, SPE Paper 14300-PA, pp. 357-360.

* cited by examiner

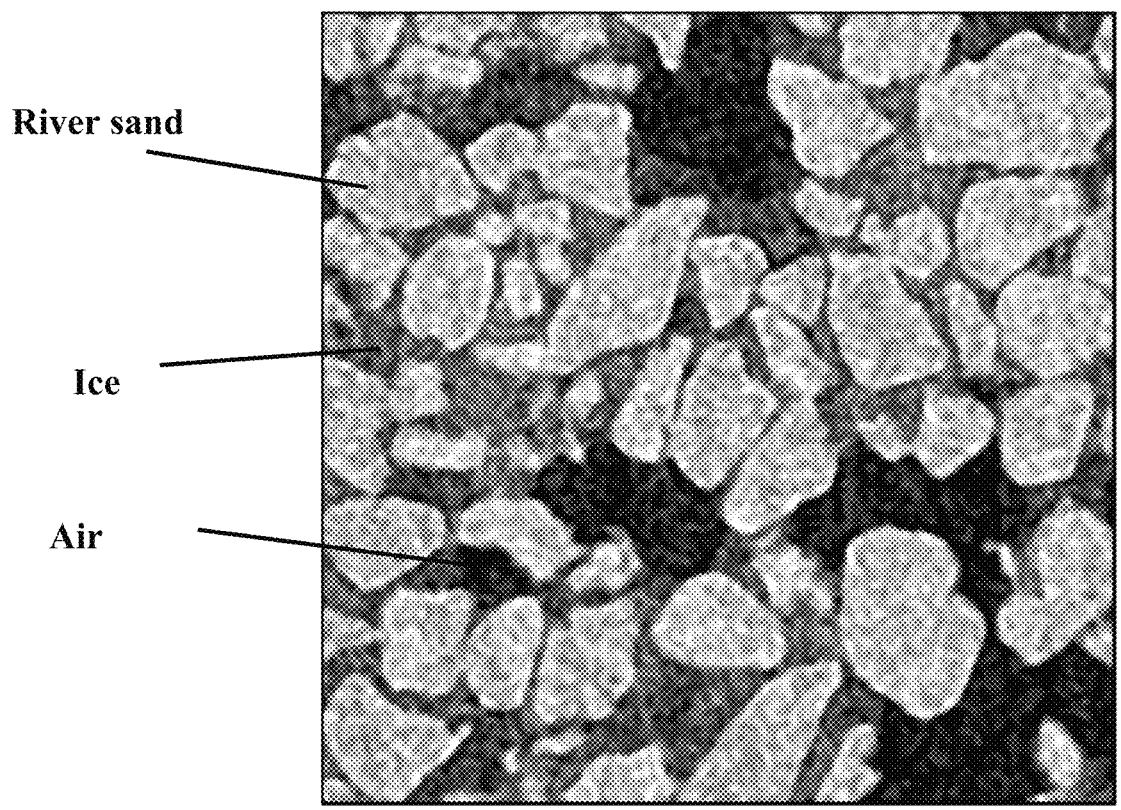

METHOD FOR EXAMINING SAMPLES OF UNCONSOLIDATED POROUS MEDIA

The invention relates to studying samples of unconsolidated porous media and may be used for determining open or closed porosity, pore size distribution, specific surface, spatial distribution of ice and/or gas hydrate inclusions in a porous space of samples, determining the size of inclusions, etc.

Most methods for studying properties of porous structures, in particular petrophysical properties of rocks, have been developed for consolidated materials (Dobrynin V. M., Vendelshtein B. Yu., Kozhevnikov D. A., Petrophysics (Physics of Rocks), Moscow: "Oil and gas" I. M. Gubkin Russian State University of Oil and Gas, 2004-368 p, ISBN 5-7246-0295-4; Gudok N. S., Bogdanovich N. N., Martynov V. G. Determining physical properties of oil-water-containing rocks, Moscow: OOO "Nedra-BusinessCenter", 2007-592 p, ISBN 978-5-8365-0298-0). To study weakly cemented rocks, special equipment and modifications of the known methods are required in order to preserve the structure and volume of a sample (U.S. Pat. No. 4,587,857, Method for mounting poorly consolidated core samples). The necessity to treat samples with some artificial cement appears, thus disturbing the in situ properties (U.S. Pat. No. 3,941,191, Method of consolidating unconsolidated or insufficiently consolidated formations). Methods of study are also known which envisage freezing of samples of unconsolidated porous media prior to examining their properties (see, for example, O. Torsaeter, The effect of freezing of slightly consolidated cores, SPE Formation Evaluation, 1987, v.2, N 3, p.357-360).

However these studies do not make it possible to identify intra-pore ice and hydrate inclusions that are the natural cement for an unconsolidated material, due to their low contrast rate, that in turn results in inaccuracies in determining characteristics of the pore space.

The method provides distinct separation (visualization) of ice and/or buildups from a solid matrix of an unconsolidated porous material by improving contrast of the cementing material (ice/hydrate buildups), which allows to calculate characteristics of a porous material and to estimate spatial distribution and concentration of ice and/or hydrate buildups in the pore space with the use of analysis of X-ray images.

The method comprises preliminary freezing a sample of an unconsolidated porous medium and providing a contact of the frozen sample and a frozen solution of an X-ray contrast agent at subzero temperatures. After saturation of the sample with ions of the contrast agent the sample is scanned by X-ray micro Computed Tomography (micro-CT) at subzero temperatures. The obtained micro-CT images and three-dimensional distribution and concentration of ice and/or gas hydrates inclusions, open and closed porosity, pore size distribution, specific surface area for the sample are determined.

The X-ray contrast agent is a water soluble composition containing a chemical element with high level of attenuation of X-ray radiation.

The chemical element with high level of attenuation of X-ray radiation is an element with high atomic weight, and the water soluble composition is a salt or an oxide.

The element with high atomic weight is a heavy metal selected from the group of elements Pb, Ba, Sr, Ra and etc.

The contact of the frozen sample with the frozen solution of the X-ray contrast agent is carried out at temperature below ice/gas hydrates melting in a porous space of the sample, preferably at temperatures from −7° C. to −10°.

Preliminary the frozen rock sample and the frozen solution of the X-ray contrast agent may be kept at a temperature from −7° C. to −10° C. till stabilization of temperature over the sample.

The X-ray micro Computed Tomography is carried out at a temperature below ice/gas hydrates melting in a porous space of the sample, preferably at a temperature from −7° C. to −10° C.

The disclosure is illustrated by FIG. 1 showing a fragment of a two-dimensional slice of a three-dimensional digital model of unconsolidated river sand cemented with ice. The image was obtained by X-ray computed microtomography conducted at temperature of −10° C. with the use of an X-ray contrast agent.

The method of X-ray microtomography is based on reconstructing spatial distribution of linear attenuation coefficient (LAC) in thin layers of a sample under study with the use of computer processing of X-ray projection in various directions along the layer being studied.

Value of LAC ($\mu$) in each material depends on chemical composition, density of the substance and radiation energy:

$$\mu = \mu_m \rho,$$

where $\mu_m$ is a mass attenuation coefficient under the action of X-ray radiation (cm$^2$/g), $\rho$ is density (g/cm$^3$).

The method is based on the effect of diffusion of ions of water-soluble compounds of elements having the capability to attenuate X-ray radiation (for example, salts of heavy metals) through a solid phase of ice/hydrate in a pore space of rocks at low temperatures, which improves contrast during X-ray microtomography al low (subzero) temperatures of ice/hydrate.

Suitable X-ray contrast agents are water-soluble compounds containing elements with a big atomic number, for example, salts of heavy metals (Pb, Ba, Sr, Ra, etc.). As a salt of a heavy metal, a soluble salt is selected in accordance with the table of solubility of inorganic compounds in water. Such salts may be: $Pb(NO_3)_2$, $BaCl_2$ and others.

As an example, a frozen 1% solution of $Pb(NO_3)_2$ was used for improving X-ray contrast of ice/hydrate as a source of ions of lead for diffusion through a solid phase of ice/gas hydrate at subzero temperatures.

Saturation of ice with a salt of a metal results, for example, in a decrease of the temperature of the ice-water phase transition, in turn, this may result in thawing of the sample at temperatures below 0° C. (the temperature of the ice-water phase transition for distilled water at the normal pressure). On the other hand, with decrease of temperature, rate of diffusion of ions slows down, leading to increasing the time of contact for saturation of the sample with ions. In the general case, temperature at contact of a sample with frozen solution should be lower than the temperature of the ice-water phase transition or gas hydrate-water in the sample.

A sample of unconsolidated porous medium and a prepared 1% solution of $Pb(NO_3)_2$ are frozen at a temperature of −15° C.--20° C. and after that the frozen solution and the frozen sample are transferred into a refrigerating chamber with temperature of about −7° C. where they are kept till stabilization of temperature. After that, the sample is placed onto the frozen solution, i.e. their direct contact is provided. The frozen sample in contact with the frozen solution is kept under isothermal conditions (constant temperature of about −7° C.) for 7 days. During that time, diffusion saturation of the frozen rock sample with ions of a heavy metal takes place. Upon the end of saturation, the contact of the sample with the frozen solution is cleaned and the sample is ready for scanning by X-ray tomograph at subzero temperatures.

The sample is studied with the use of a low-temperature add-on device (Cooling stage, http://www.skyscan.be/products/stages.htm) on an X-ray microtomograph. The sample was scanned at the temperature of about −10° C. in order to avoid thawing of ice.

The result of scanning is a three-dimensional digital model of the core whose analysis makes it possible to determine petrophysical characteristics of an unconsolidated rock, as well as distribution of ice/gas hydrate in the pore space, etc.

The invention claimed is:

1. A method for studying unconsolidated porous media comprising:
   preliminary freezing a sample of an unconsolidated porous medium,
   providing a contact of the frozen sample of the unconsolidated porous medium and a frozen solution of an X-ray contrast agent at subzero temperatures,
   after saturation of the frozen sample with ions of the X-ray contrast agent scanning the frozen sample by X-ray micro Computed Tomography (micro-CT) at subzero temperatures,
   analyzing a micro-CT image obtained by the scanning and determining three-dimensional distribution and concentration of ice and/or gas hydrates inclusions, open and closed porosity, pore size distribution, specific surface area for the sample.

2. The method of claim 1, wherein the X-ray contrast agent is a water soluble composition containing a chemical element with high level of attenuation of X-ray radiation.

3. The method of claim 2, wherein the chemical element with high level of attenuation of X-ray radiation is an element with high atomic weight, and the water soluble composition is a salt or an oxide.

4. The method of claim 3, wherein the element with high atomic weight is a heavy metal selected from group of elements Pb, Ba, Sr, Ra.

5. The method of claim 1, wherein the contact of the frozen sample of the unconsolidated porous medium with the frozen solution of the X-ray contrast agent is carried out at a temperature below ice/gas hydrates melting in a porous space of the sample.

6. The method of claim 5, wherein the contact of the frozen sample of the unconsolidated porous medium with the frozen solution of the X-ray contrast agent is carried out at temperatures from −7° C. to −10° C.

7. The method of claim 1, wherein the frozen sample of the unconsolidated porous medium and the frozen solution of the X-ray contrast agent are preliminary held at temperatures below ice/gas hydrates melting in a porous space till temperature stabilization.

8. The method of claim 7, wherein the frozen sample of the unconsolidated porous medium and the frozen solution of the X-ray contrast agent are preliminary held at temperatures from −7° C. to −10° C.

9. The method of claim 1, wherein the X-ray micro Computed Tomography is carried out at a temperature below ice/gas hydrates melting in a porous space of the sample.

10. The method of claim 9, wherein the X-ray micro Computed Tomography is carried out at temperatures from −7° C. to −10° C.

* * * * *